United States Patent
Mednikov

(10) Patent No.: US 6,537,493 B1
(45) Date of Patent: Mar. 25, 2003

(54) STERILIZATION APPARATUS

(75) Inventor: Mark Mednikov, Jerusalem (IL)

(73) Assignee: Microlizer Ltd., Migdal Haemek (IL)

( * ) Notice: Subject to any disclaimer, the term of this patent is extended or adjusted under 35 U.S.C. 154(b) by 202 days.

(21) Appl. No.: 09/655,834

(22) Filed: Sep. 6, 2000

(51) Int. Cl.⁷ .................................................. A61L 2/00
(52) U.S. Cl. ................................ 422/21; 422/1; 422/26; 219/686
(58) Field of Search ................................ 422/1, 21, 25, 422/26; 219/686, 695, 748, 749

(56) References Cited

U.S. PATENT DOCUMENTS

| | | | |
|---|---|---|---|
| 3,577,207 A | * 5/1971 | Kirjushin | 219/686 |
| 3,753,651 A | * 8/1973 | Boucher | 219/738 |
| 4,952,763 A | * 8/1990 | Fritz | 219/697 |
| 5,098,665 A | 3/1992 | Katschnig et al. | 422/108 |
| 5,124,125 A | * 6/1992 | Brent | 422/21 |
| 5,246,674 A | 9/1993 | Katschnig et al. | 422/302 |
| 5,320,804 A | 6/1994 | Zakaria et al. | 422/21 |
| 5,322,603 A | 6/1994 | Kameda et al. | 204/158.2 |
| 5,728,310 A | * 3/1998 | Ice et al. | 219/679 |
| 5,879,643 A | * 3/1999 | Katschnig et al. | 250/574 |

\* cited by examiner

*Primary Examiner*—Krisanne Thornton
(74) *Attorney, Agent, or Firm*—Blank Rome Comisky & McCauley LLP

(57) ABSTRACT

The present invention includes a method and apparatus for sterilization of medical wastes by exposing them to microwave energy. The microwaves are generated and directed through a wave-guide configured as a hollow duct, such that they are supplied to the interior of a treatment chamber from opposite directions causing their collision within the chamber.

10 Claims, 12 Drawing Sheets

STERILIZATION APPARATUS

FIELD OF THE INVENTION

The present invention relates to sterilization of wastes, primarily to sterilization of medical wastes, e.g. bandages, needles, disposable syringes, gloves, test tubes, blades etc.

More particularly the invention concerns sterilization treatment of wastes within a sealed container with the aim of microwave energy, produced by a magnetron source.

It should be emphasized however, that the present invention is not limited strictly to the sterilization of medical wastes and it can be successfully employed in many other applications as well, in which sterilization treatment of wastes is required.

BACKGROUND OF THE INVENTION

Environmentally safe disposing of wastes is expensive measure, since relatively economical means like refusing, polygonal burial, incineration is either forbidden or are insufficiently safe.

Therefore numerous devices for disinfection medical wastes have been devised for treatment of medical wastes locally. These devices employ various sources of energy for treatment and the further description will be referred to those sterilization devices, which are provided with autonomous sources of microwave energy.

Among these dedicated devices one can mention, for example, device for heating of articles and organisms, as described in U.S. Pat. No. 5,098,665. This device contains microwave emission device, consisting of a plurality of magnetrons emitting microwave radiation into a sterilization chamber. The magnetrons are configured to enable the output density be uniformly distributed over the interior of the sterilization chamber, thus enabling the infected material to be uniformly and completely sterilized.

The other known microwave sterilization apparatus is disclosed in U.S. Pat. No. 5,246,674. This apparatus includes an injection unit by which water or other liquid is introduced into the material to be treated depending on the water content of the material.

Still further apparatus for controlled microwave heating apparatus is described in U.S. Pat. No. 5,320,804. The apparatus comprises a microwave chamber with a turntable that is capable to oscillate and rotate, a source of microwave radiation and pressure responsive controller, capable to control the source of microwave radiation.

In U.S. Pat. No. 3,222,603 is disclosed an apparatus in which infectious medical wastes are treated by microwaves during an initial stage and then by hot air supplied to treatment chamber and circulating therein.

The main disadvantage of the known in the art sterilization devices is associated with the fact, that they require excessive treatment time for completing the process. The reason for this lies in the electro physical construction of the wave-guides, employed in these devices. The known in the art microwave sterilization apparatuses employ wave-guides defined by opened configuration, extending in one direction towards the treatment chamber. In accordance with the present invention it has been empirically revealed, that this configuration is not the most efficient one and microwave energy can be utilized more efficiently, when the wave-guide has closed configuration, in which the waves can propagate from two opposite directions towards each other and collide in a common point, located within the sterilization area. It has been found, that the collision is accompanied by producing of pick of energy, which is released with the microwaves and therefore this configuration of the wave-guide renders the whole process more efficient and economical, since the time, required for the sterilization treatment sufficiently shortens.

The further disadvantage of the known sterilization devices is their relatively large size and complexity, and therefore inconveniency for use in small clinics and other medical institutions.

Still further disadvantage of the prior art sterilization devices lies in the fact, that they usually don't recycle the hot air releasing from the treatment chamber. As a rule this air exits directly into atmosphere and since the exhausted air has been in direct contact with the wastes it pollutes the environment.

Therefore despite the fact that different sterilization devices for treatment of medical wastes have been devised there still exists a need for a new and improved device, which is compact, simple, inexpensive and efficient.

OBJECT OF THE INVENTION

The object of the present invention is to provide a new and improved microwave sterilization apparatus, which sufficiently reduce or overcome the above-mentioned drawbacks of the known in the art sterilization apparatuses.

In particular the main object of the present invention is to provide a new and improved sterilization apparatus, enabling more efficient and fast sterilization.

The further object of the present invention is to provide a new sterilization apparatus, which is inexpensive and which has simple and compact construction.

The third object of the present invention is to provide a new and improved sterilization apparatus, which enables recycling of the air, exiting the apparatus and thus is environmentally friendly.

The above and other objects and advantages of the present invention can be achieved in accordance with the following combination of its essential features, referring to different embodiments thereof.

In accordance with the main embodiment of the invention the apparatus comprises:

a) a hermetically closable treatment chamber, configured as microwave-transparent, pressure retaining vessel, in which said medical wastes are received and undergo the sterilization process, b) a source of microwave energy, substantially a magnetron with a wave-guide for directing the microwaves, emanated by said source to the interior of the treatment chamber, c) an electrical power supply means operatively coupled with the magnetron, said power supply means is responsible for establishing and maintaining of microwave radiation, emanating from the magnetron, d) an appropriate control and instrumentation means for monitoring the electrical parameters of said power supply means, e) a liquid medium reservoir, which is in fluid communication with the interior of the treatment chamber to supply the liquid medium to the interior of the treatment chamber to produce steam upon exposure the said liquid medium to the microwave energy, f) a steam release means, which is in fluid communication with the interior of the treatment chamber, said steam release means is adapted to control pressure within the chamber during the sterilization process, wherein said wave-guide comprises a hollow duct communicating with the interior of the treatment chamber, said duct is configured as closed path directing the microwaves produced by the magnetron first in two opposite directions and then in two approaching directions to enable their collision in a meeting point within the treatment chamber.

In a further embodiment the wave-guide is configured as a body, defined by a mirror symmetry and by a plane of symmetry, wherein said treatment chamber is located with respect to the wave-guide in such a manner, that its plane of symmetry lies in the treatment chamber.

In the third embodiment the said treatment chamber comprises an outer tubular shell, which is receivable within the wave-guide, said shell is provided with at least two opposite through-going windows to enable passing the microwaves therethrough, said shell is lined by a microwave transparent lining.

In accordance with the other embodiment the apparatus is provided with a collection bin for collecting the sterilized wastes.

In a still further embodiment the treatment chamber is located above the collection bin and is provided with an input door for opening the chamber and loading the wastes thereinto and with an output door for unloading the sterilized wastes therefrom.

As per another embodiment the input door and the output door is operated by a dedicated opening and closing mechanism, said mechanism is capable to close the respective door and to seal the treatment chamber tightly.

In an additional embodiment the tubular shell is configured substantially as a cylinder having its longitudinal axis located preferably within the plane of symmetry of the wave-guide.

According to yet another embodiment the tubular shell is made as an integral part of the wave-guide.

In still further embodiment, referring to a method for sterilization of wastes by exposing them to microwave energy it comprises the following sequence of steps:

g) Placing said wastes within a treatment chamber, configured as microwave-transparent, pressure retaining vessel h) Generating of microwaves, substantially by a magnetron source i) Directing said microwaves through a hollow wave-guide from the magnetron source to the interior of the chamber j) Exposing the wastes placed within the chamber to the microwave energy.

wherein said microwaves are supplied to the interior of the treatment chamber from two opposite directions to cause their collision within the chamber.

In the further embodiment the step of directing of the microwaves is carried out along a closed path first in two opposite directions and then in two approaching directions to bring the microwaves approaching the chamber from two opposite sides to collision within the treatment chamber.

The present invention in its various embodiments has only been summarized briefly. For better understanding of the present invention as well of its advantages, reference will now be made to the following description of its embodiments with reference to the accompanying drawings.

DETAILED DESCRIPTION OF SPECIFIC EMBODIMENTS

Figure 1:
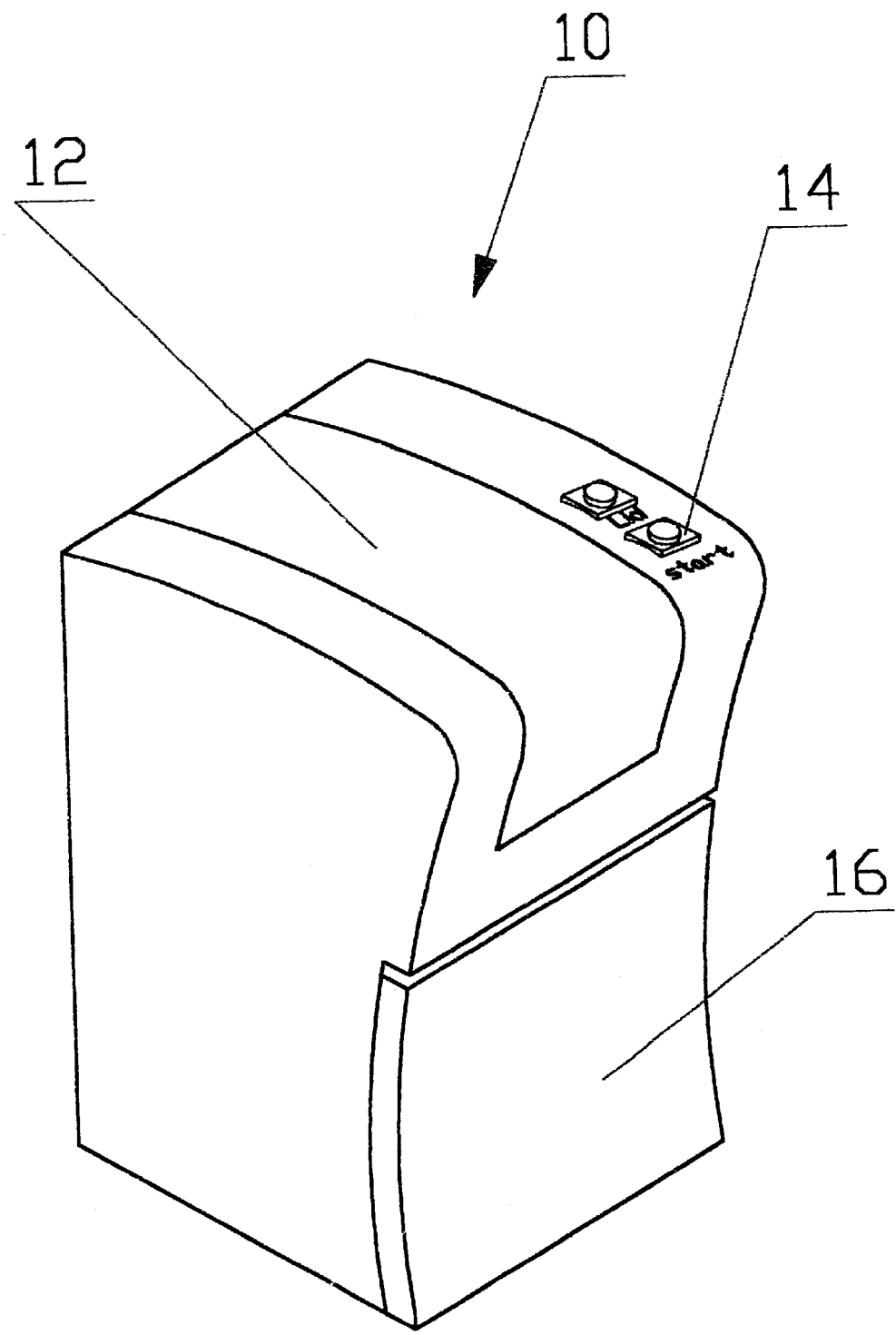
FIG. 1 is general isometric view of the apparatus of the invention.

With reference to FIG. 1 the apparatus 10 of the invention comprises a housing configured substantially as a substantially parallelepiped box, having upper cover 12 with a main knob 14 for running the apparatus. Within the housing are mounted all the components of the apparatus. A front cover 16 mounted on the lower frontal side of the hosing enables access to the interior of the housing and evacuation of the treated wastes.

Figure 2:
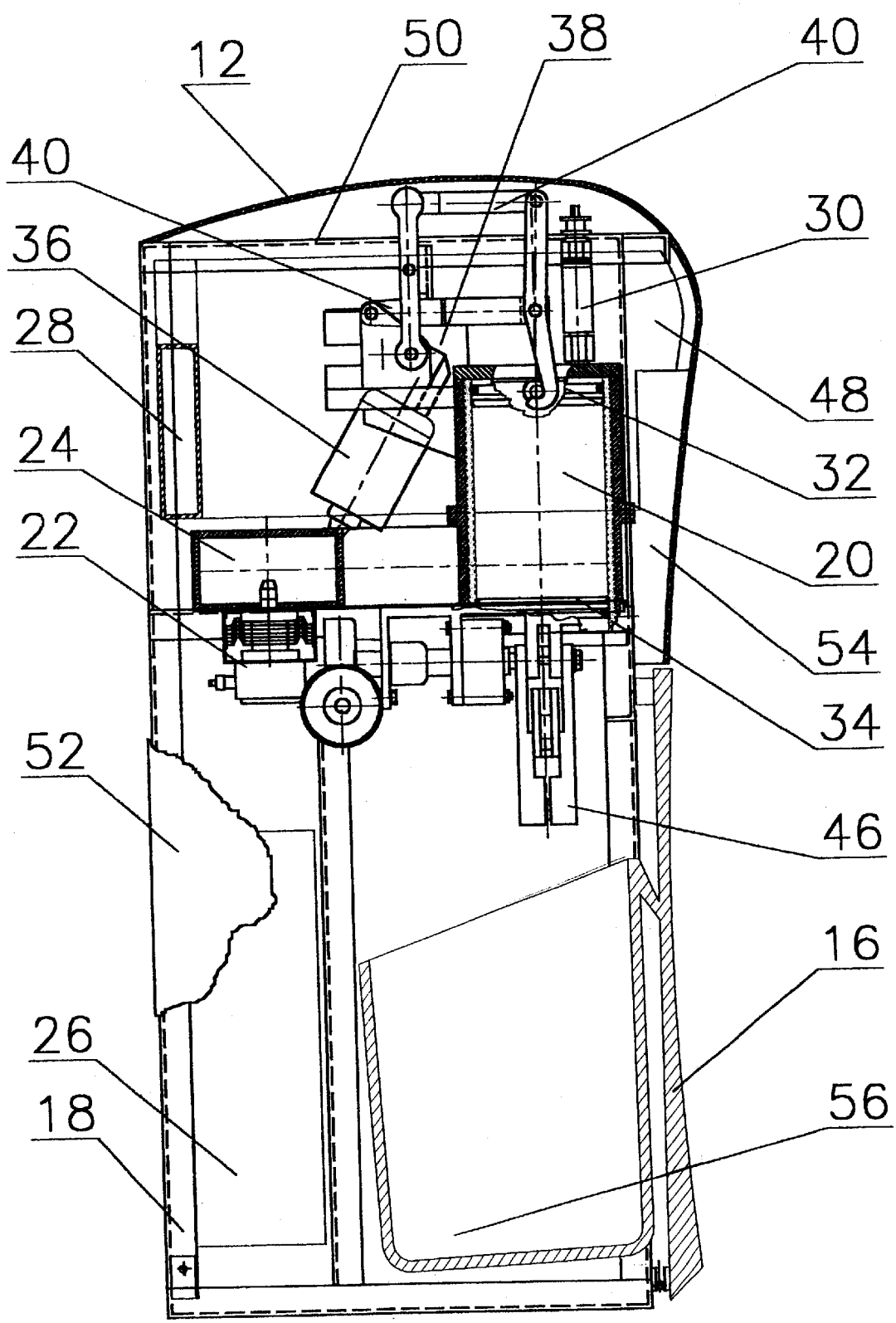
FIG. 2 is cross-sectional view of the apparatus, showing its main component.

As seen in FIG. 2 within the housing resides a frame 18 carrying the main components of the apparatus. These components include a treatment chamber 20 for receiving medical wastes, a magnetron 22, a wave-guide 24 for directing the microwaves from the magnetron to the interior of the treatment chamber, a power supply 26, operatively coupled with the magnetron, a reservoir 28 for supplying a liquid fluid into the treatment chamber and a steam release valve 30, which controls the pressure within the chamber during the sterilization process. It is now shown specifically, but should be understood, that there are provided also appropriate control and instrumentation means for monitoring the electrical parameters of the power supply. During the sterilization process the treatment chamber is tightly closed by an upper input door 32 and by a lower output door 34. Each door is provided with its own closing and opening mechanism and can be independently opened and closed. The mechanism for opening and closing the doors comprises a motor, which is operatively coupled through a reductor to a lever rod assembly. Each lever road assembly includes a traction rod TR, connected to the respective door for pushing or pulling thereof.

In FIG. 2 is seen, that the input door 32 is operated by the dedicated mechanism, consisting of motor 36, reductor 38 and lever rod assembly 40. The output door 34 is operated by the dedicated mechanism, consisting of motor 42, reductor 44 and lever rod assembly 46.

Figure 3:
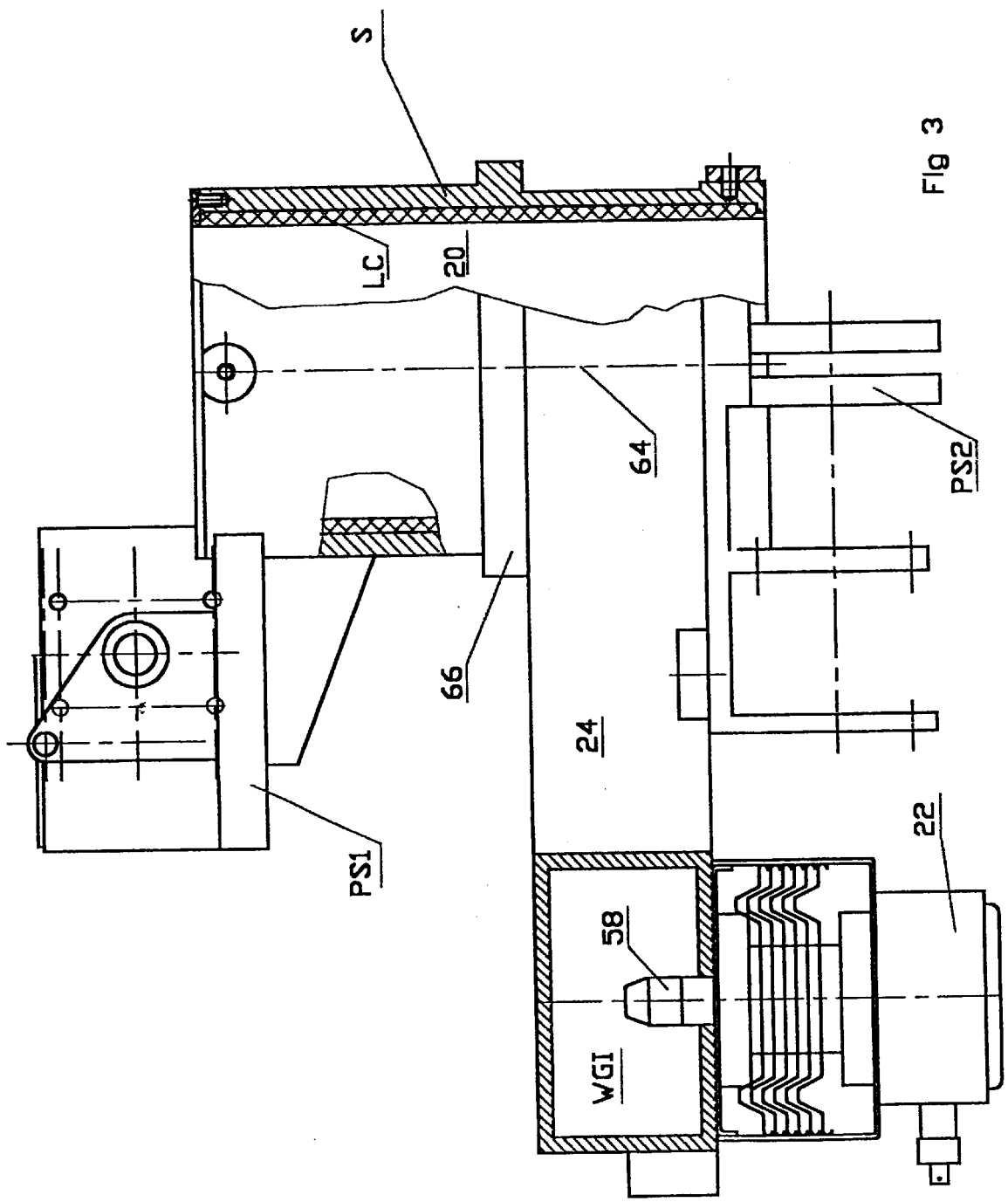
FIG. 3 is partial cross-section taken through the magnetron source and treatment chamber.
Figure 4:
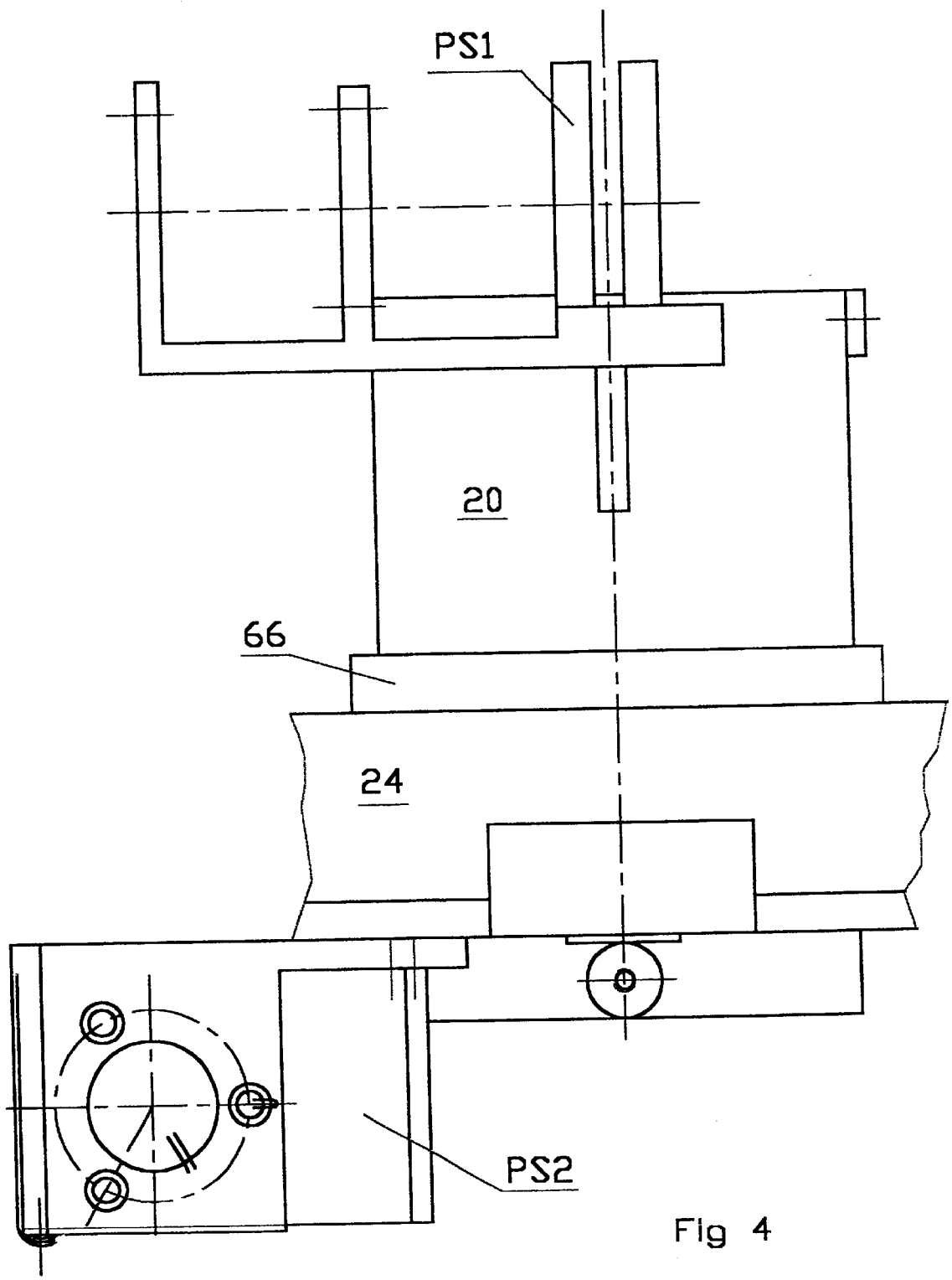
FIG. 4 is partial view, showing connections and fittings for attachment of upper and lower door operating mechanism.

With reference to FIGS. 3, 4 it is seen that there are provided means for attachments the lever rod assemblies. Those means comprise brackets formed as partitioned shelves PS1 and PS2. It can be seen that shelves PS1 and PS2 have similar design but direction of partitions of shelve PS1 is perpendicular to the direction of partitions of shelve PS2. By virtue of this provision it is possible to make the whole mechanism more compact, since lever rod assembly and respective motor do not extend in the same direction.

Within the housing a room 48 is provided for a pump means (not shown), capable of supplying a liquid medium, substantially water, from reservoir 28 through duct 50 and valve 30 to the interior of the treatment chamber.

The lateral sides of the housing are closed from the outside by a sheeting 52 and the upper frontal side of the housing is closed by a sheeting 54.

Figure 10:
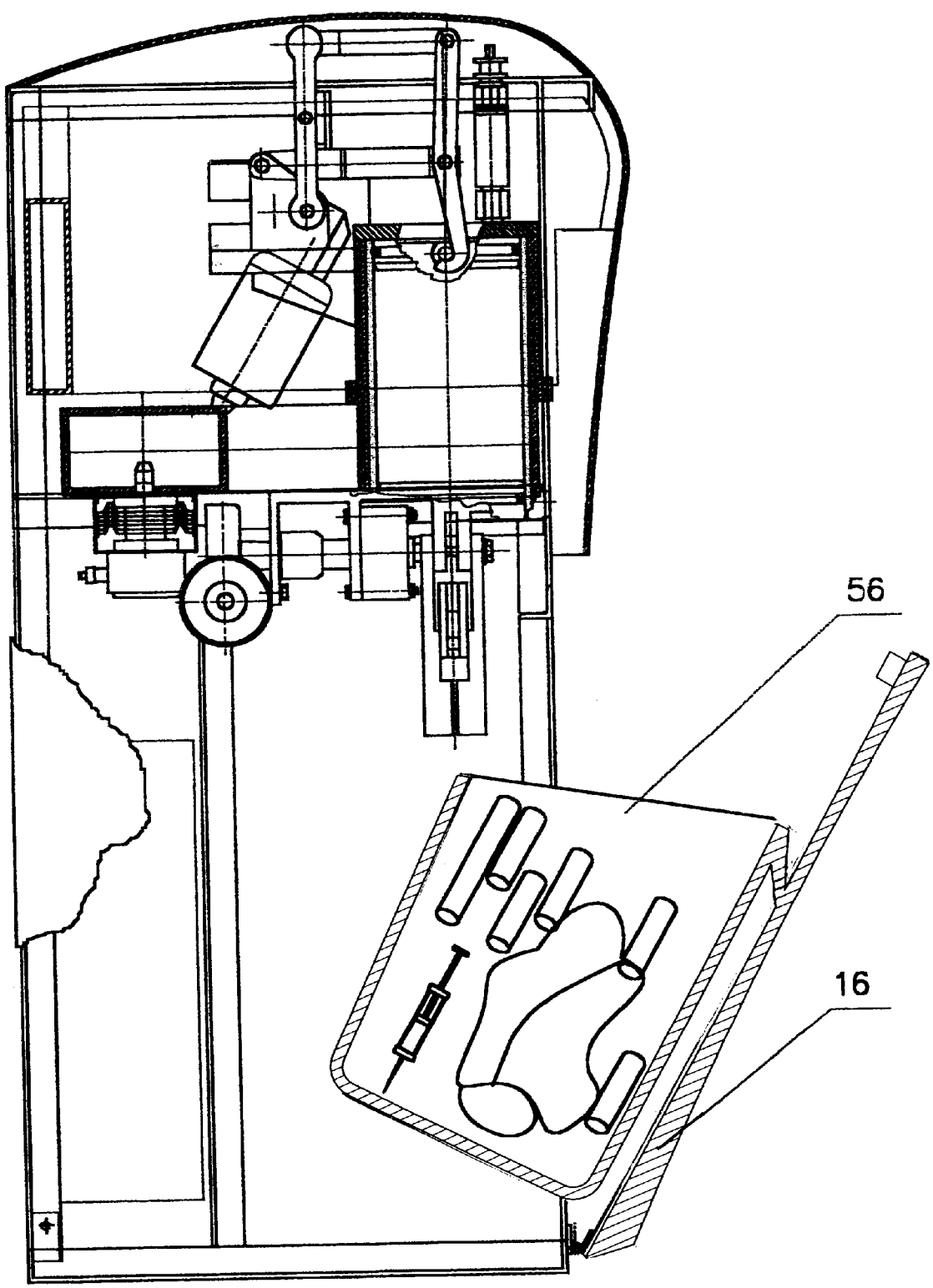
FIG. 10 is cross-sectional view of the apparatus in the position, in which the collecting bin is pivoted to unload the treated wastes outside.

Residing in the lower part of the housing a collecting bin 56 is provided. The bin is connected to the front cover 16 and thus when the cover is in its pivoted opened position the bin can be accessed from the outside and its content can be evacuated. The opened position of the bin is shown in FIG. 10.

In brief the principle of operation of the apparatus is as follows. Once the knob 14 is pushed, the upper cover is closed and the input door hermetically closes the chamber. Power supply energizes the magnetron and it generates microwaves with frequency 2450 MHz, which are supplied through the wave-guide to the treatment chamber. In FIG. 2 parallel arrows schematically designate the microwaves propagating through the wave-guide. The microwaves collide with the water molecules within the treatment chamber and transfer them energy, which converts water into steam and the steam efficiently sterilizes the content the chamber.

It can be appreciated, that the treatment chamber should be transparent to the microwave energy and at the same time capable to keep pressure developing in the chamber due to conversion of water to steam.

To comply with this requirement the chamber is designed as pressure-retaining vessel having its outer tubular shell S made of steel or other material capable to keep pressure of 10–15 atm. (see FIG. 3). To maintain the pressure within the chamber the input and the output doors are provided with appropriate sealing means, e.g. O-rings.

As seen in FIG. 3 within the shell resides an inside tubular lining cylinder LC made of material, having dielectric loss factor $\epsilon''=10^{-6}-10^{-7}$ and thus transparent to the microwaves. As suitable material once can use Teflon or glass. The shape of the lining cylinder matches the shape of the shell. In order to secure the lining within the shell the outside diameter of the lining is kept very close to the inside diameter of the shell.

The above principle of operation is known and is employed in many prior art sterilization apparatuses. However, in contrast to the conventional apparatuses in the present apparatus the microwave energy is supplied to the chamber in such a manner, that it effects much more efficient and fast sterilization is achieved.

With reference to FIGS. 3,5 it will be explained now the construction of the new wave-guide, enabling supply of the microwave energy in a concentrated fashion, resulting in enhancement of the sterilization action.

In FIG. 3 is seen that wave-guide 24 is configured as a hollow duct having its interior WGI into which protrudes an anode emitter 58; emanating the microwaves.

In practice in order to make the whole apparatus compact and portable it is very convenient to use for generating the microwaves the commercially available small magnetron generators, which are employed in domestic microwave ovens. As an example of a suitable magnetron generator one can mention model MWO 1420 B used in domestic microwave ovens manufactured by Sun Rise Ltd., Japan. This generator operates at frequency 2450 MHz and its output power is 870–1000 wt. The rest of electrical parameters of this generator are:

Filament voltage 3.3 V

Filament current 10.5 A

Peak anode voltage 4.1 kV

Average anode current 300 mA

Peak anode current 1.2 A.

Figure 5A:
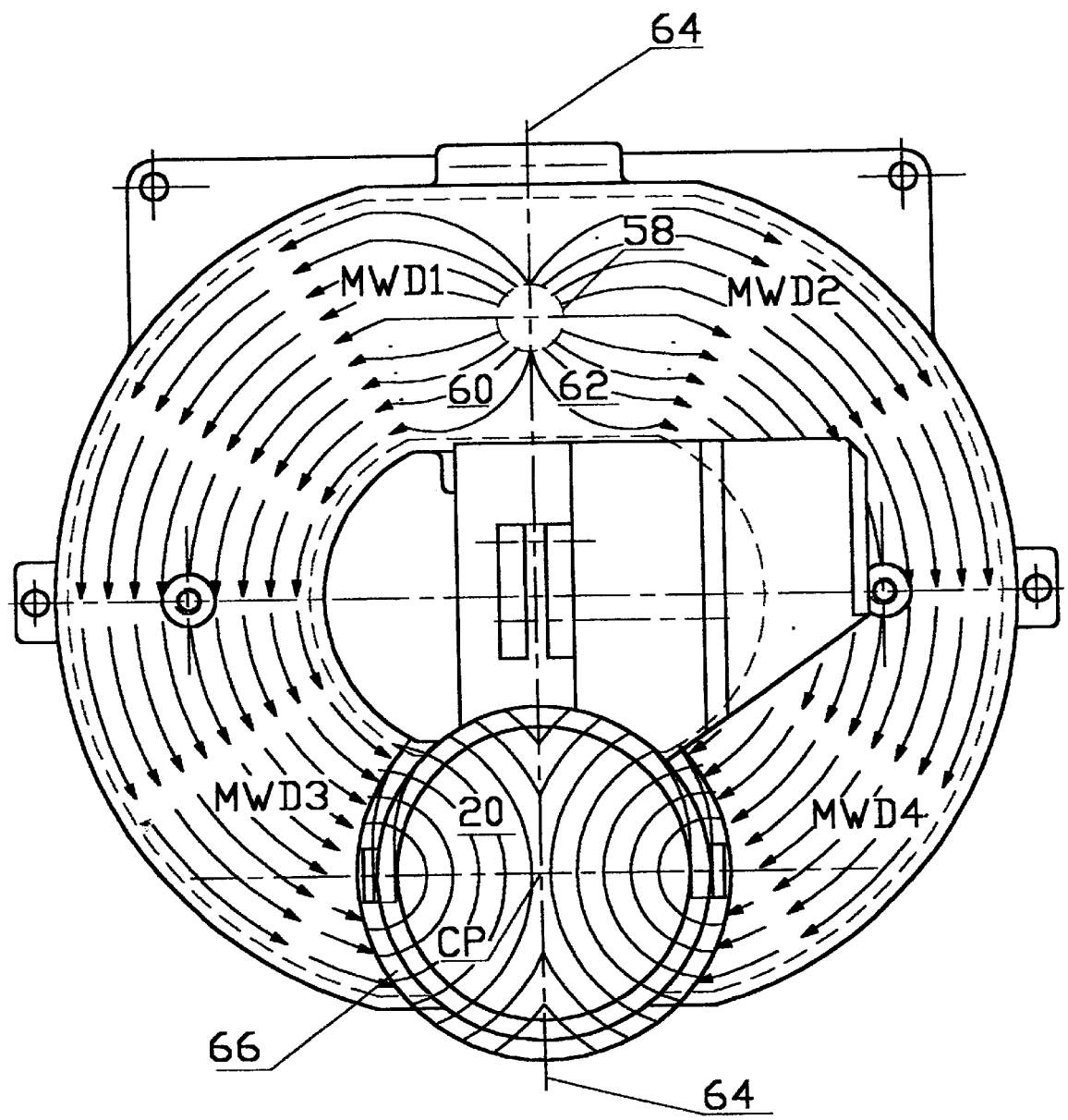
FIG. 5a is upper elevation of the wave-guide with the treatment chamber received therein.
Figure 5B:
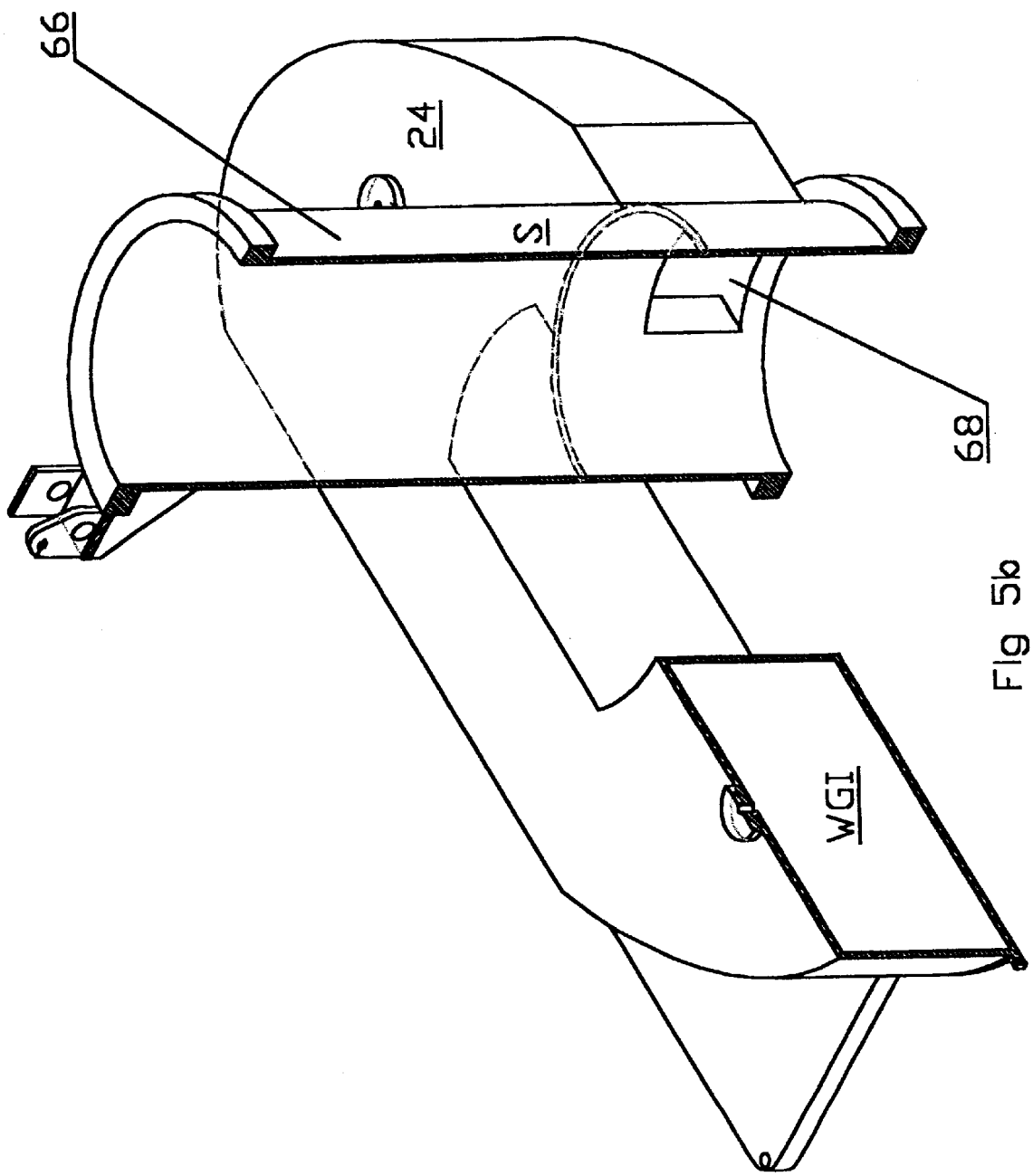
FIG. 5b is isometric partially cross-sectioned view of the wave-guide.
Figure 5C:
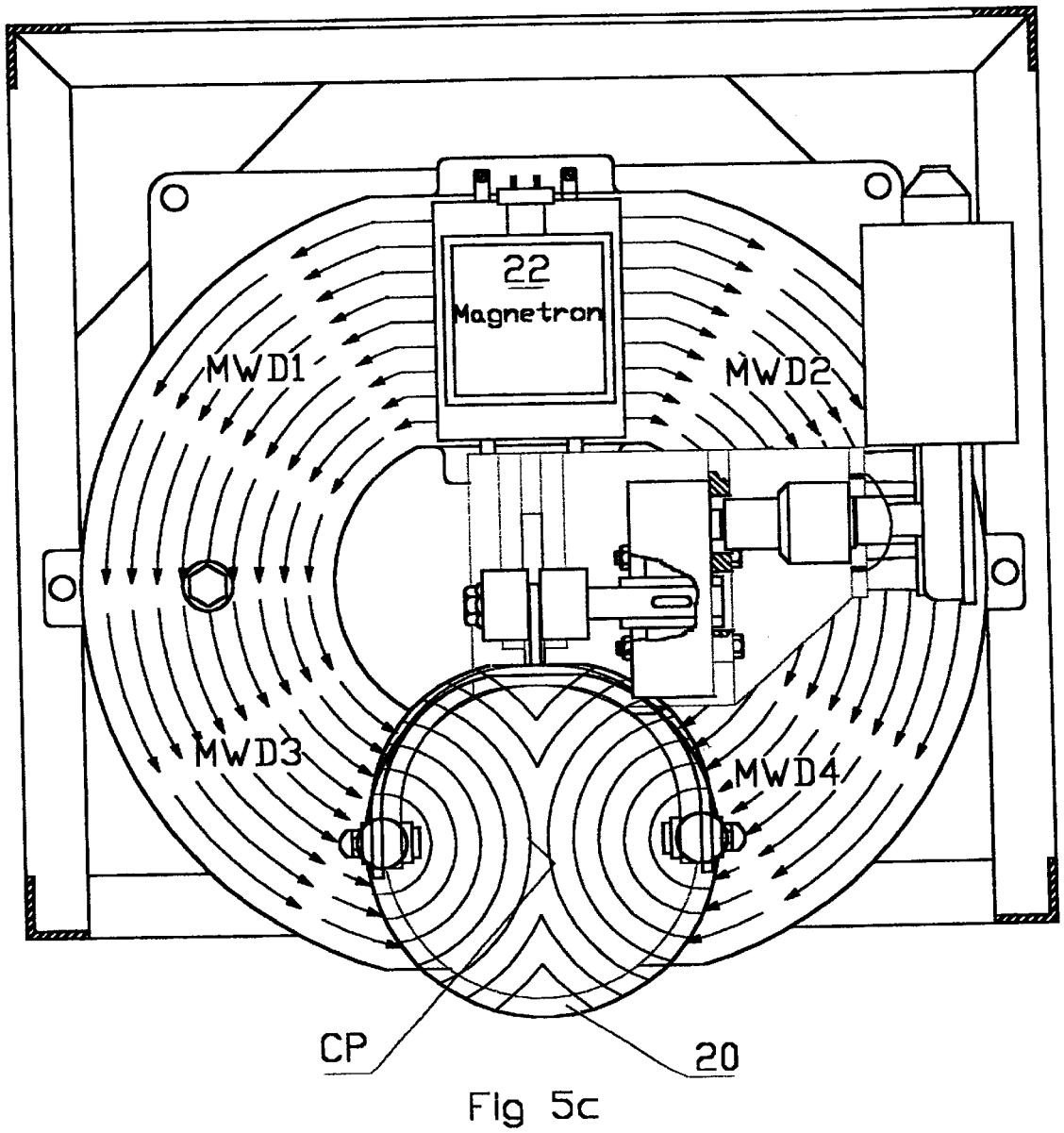
FIG. 5c is schematic presentation of the microwaves progagating along the wave-guide along closed path
Figure 6:
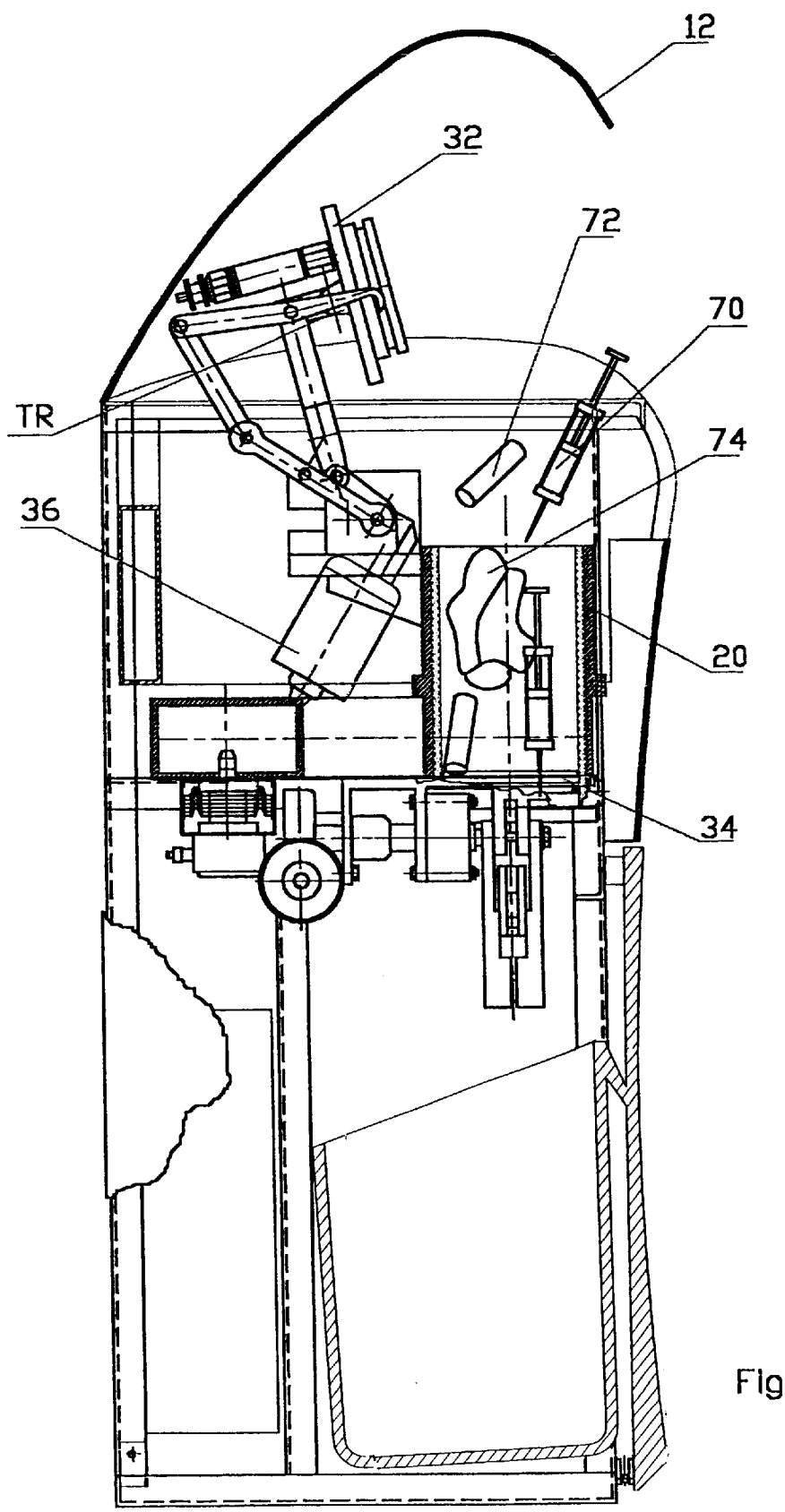
FIG. 6 is cross-sectional view of the apparatus in the position, in which medical wastes are loaded in the treatment chamber.

As best seen in FIGS. 5a, 5b, 5c the wave-guide duct has circular-like configuration and consists of two adjacent C-like sections 60,62, adjoining to each other along a plane 64. The sections have identical shape and therefore the whole wave-guide can be defined as a body, having mirror symmetry with the plane 64 being its plane of mirror symmetry.

It can be appreciated, that by virtue of this configuration the microwaves originating from the emitter propagate along a closed path in the sense, that they start propagating in two opposite directions as designated by arrows MWD1, MWD2 and then proceed in two approaching directions as designated by arrows MWD3, MWD4 until they meet in a collision point CP. It is seen in FIGS. 5a, 5c, that the meeting point lies substantially within the plane of mirror symmetry.

Within the wave-guide is made opening, defined by a cylindrical wall 66. This wall is made of strong metallic material and it can be either welded to the wave-guide or be an integral part thereof. The wall constitutes an outer tubular shell S of the treatment chamber and the tubular lining cylinder LC is secured therein (it is not shown in FIG. 5b). That part of the annular wall, which resides within the wave-guide, is provided with two opposite through-going windows. One of those windows, designated at 68, is shown in FIG. 5b, By virtue of the windows the propagating microwaves pass the metallic shell and enter within the chamber along directions MWD3, MWD4 until they meet in a collision point CP within the chamber (see FIGS. 5a, 5c). In practice the outer shell slightly protrudes down from the wave-guide to ensure that the output door constitutes bottom of the treatment chamber.

It has been empirically found that by virtue of the above-described wave-guide the microwaves intensively collide within the chamber and their collision is accompanied by enhanced release of microwave energy, which sufficiently improves the sterilization efficiency.

Furthermore, since the wave-guide together with the treatment chamber constitutes an integral body, which behaves as a rising resonator a maximum standing wave with the standing wave coefficient 1.2–2 is established within the chamber. This standing wave improves absorption of the microwave energy and shortens the sterilization cycle.

Now with reference to FIGS. 7–10 functioning of the apparatus will be explained.

Figure 7:
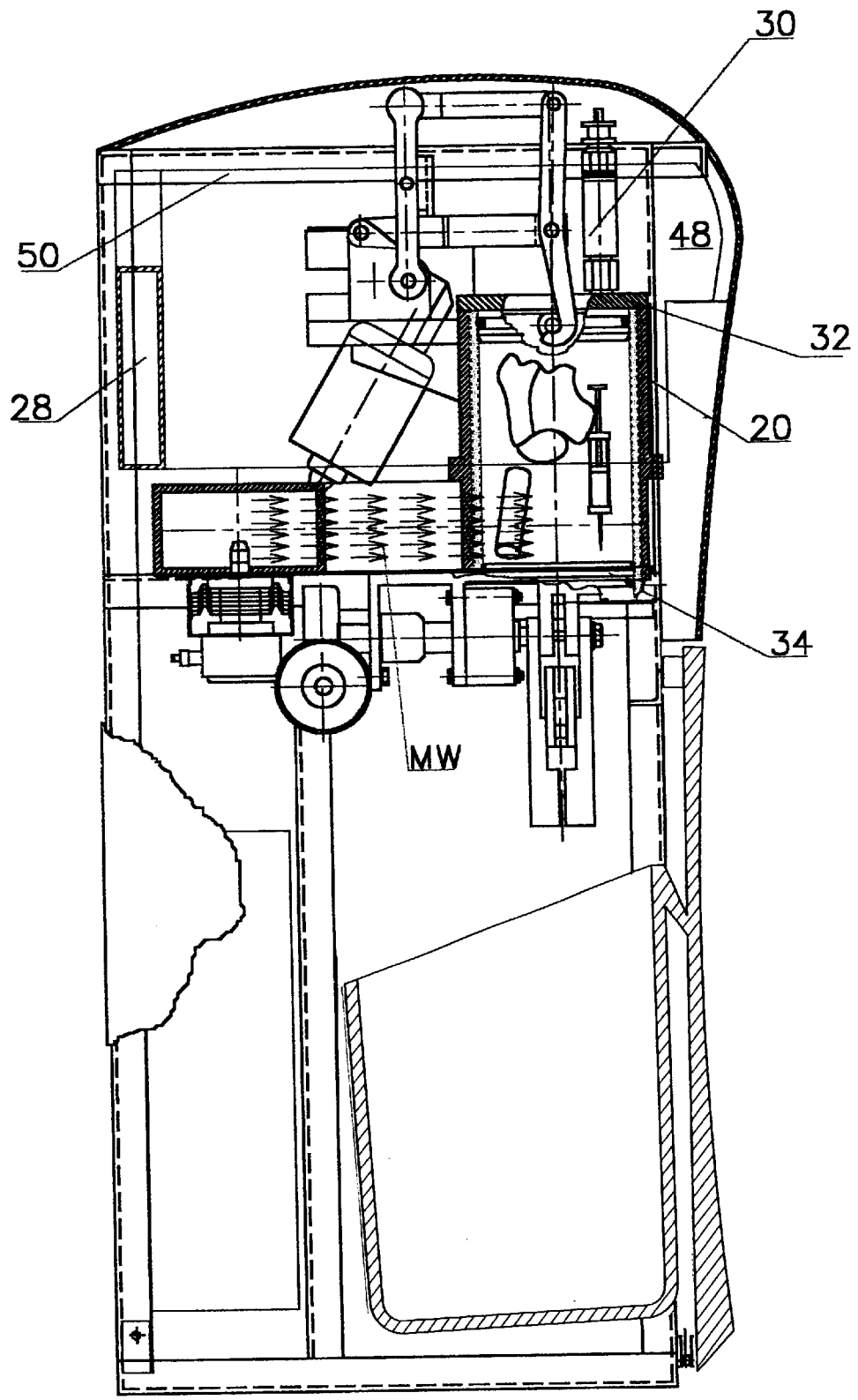
FIG. 7 is cross-sectional view of the apparatus in the position, in which the treatment chamber is closed and the wastes are exposed to the microwave energy.

FIG. 7 refers to initial stage of the treatment. In this stage the upper cover 12 of the housing is brought in its upper position to enable access to the interior of the apparatus and to the treatment chamber 20. The upper opening mechanism opens the input door 32 by virtue of traction rod TR, which is pulled by motor 36. Medical wastes, schematically shown as syringe 72, test tube 74, bandage 76 etc. are loaded in the treatment chamber. The fluid medium in the amount of about 50–100 ml is supplied by pump 48 from reservoir 28 to the chamber via duct 50 and valve 30. The lever rod assembly of the lower mechanism tightly closes the output door 34. The collecting bin is still empty and the front cover is closed.

In FIG. 7 is shown the next stage, in which the input door 32 and the output door 34 tightly seal the interior of the chamber 20. The power supply is on, the magnetron produces microwaves MW, which propagate via the wave-guide and the interior of the chamber is exposed to the microwave energy. By virtue of the microwave energy the fluid medium converts into steam and sterilization process takes place at about 130–140 degrees C. and pressure 3.5–3.8 atm.

The electrical parameters of the power supply are controlled in such a manner, that the sterilization process in terms of time, temperature and pressure in the chamber is carried according the following schedule.

Once the magnetron is energized the temperature in the chamber rises in about 20 minutes from ambient temperature up to about 60 degrees C. This temperature is kept for 20 minutes to evacuate the air, which is trapped in the chamber through valve 30. Then the temperature is increased quickly to about 120 degrees C. and then to 160 degrees C. The pressure in the chamber rises up to 4.5 atm. At this stage the release valve periodically opens to keep pressure in the chamber in the range of 4.5–3.5 atm and temperature in the range of 140–160 degrees C.

The above conditions are maintained for 2 minutes until completion of the sterilization process. The sterilization process is carried out very efficiently and fast. since release of air facilitates penetration of the steam in the wastes and because steam has good thermal conductivity.

After the sterilization cycle is completed the power supply is turned off and temperature and pressure in the chamber decreases up to ambient conditions.

Figure 8:
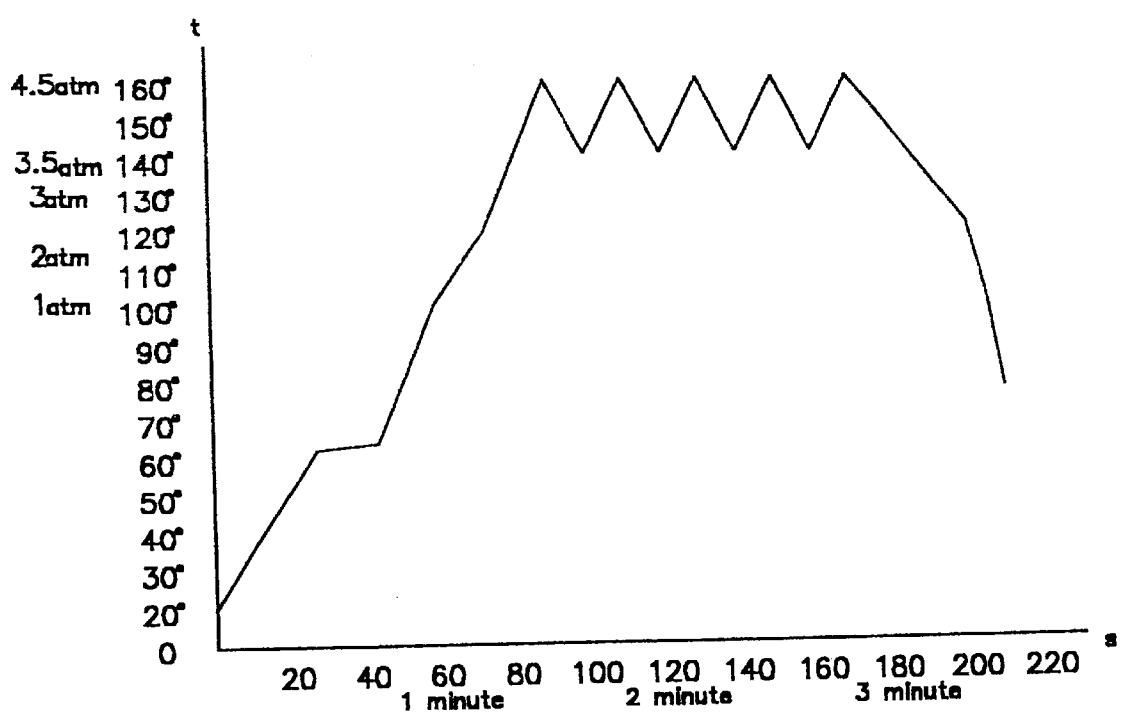
FIG. 8 is graphic representation of the dependence of temperature and pressure on time during the sterilization treatment.

In FIG. 8 the above parameters are presented graphically and it can be seen that the whole process from its beginning to the end lasts about 3 minutes due to intensive and fast heating achieved by exposing the chamber to microwave energy supplied from two opposite direction as explained above.

Figure 9:
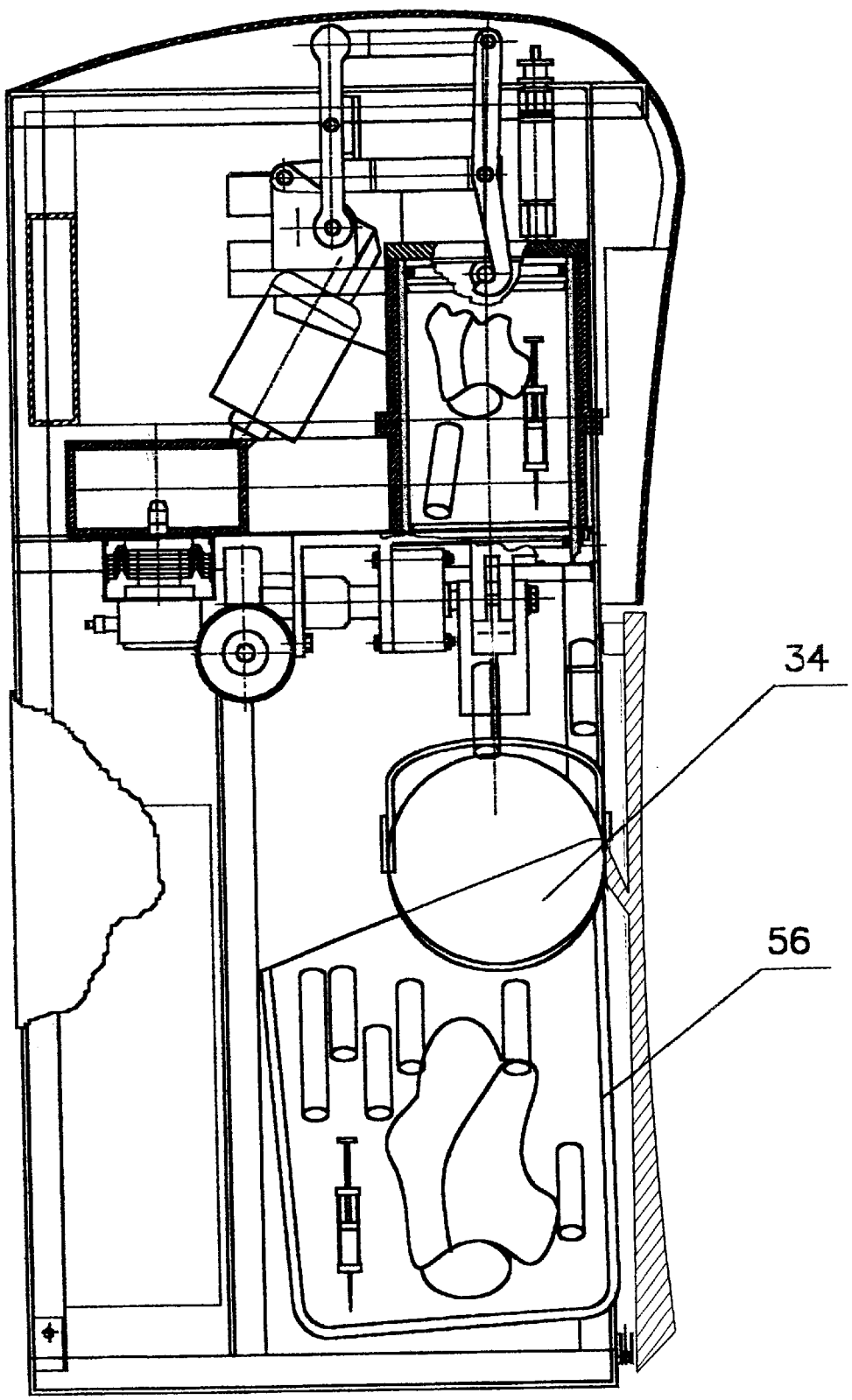
FIG. 9 is cross-sectional view of the apparatus in the position, in which the treatment is terminated and the sterilized wastes are unloaded into collecting bin.

The penultimate stage of the process is shown in FIG. 9. At this stage the lower opening mechanism opens output door 34 and the wastes fall by gravitation from the chamber into collection bin 56. Once the content of the treatment chamber is transferred into collecting bin the output door is closed again. Upon filling the bin front cover 16 is pivoted to enable access to the bin for evacuating the wastes therefrom. This stage is seen in FIG. 10. Since the wastes are already sterilized they are not dangerous for further processing.

It should be appreciated that the present invention is not limited to the above-described embodiments and that one ordinary skilled in the art can make modifications without deviation from the scope of the invention as will be defined in the appended claims.

For example, instead of above-described magnetron one can use other magnetrons, e.g. models 2M121A, 2M131, 2M130 manufactured by Hitachi. The power of the magnetron can be either more or less than the power of the above-described magnetron. The volume of the working chamber can be increased up to 2–3 liters and evacuation of wastes from the collection bin can be performed automatically.

It should also be appreciated that the features disclosed in the foregoing description, and/or in the following claims, and/or in the accompanying drawings may, both separately and in any combination thereof, be material for realizing the present invention in diverse forms thereof.

What is claimed is:

1. A sterilization apparatus, primarily for sterilization of medical wastes by exposing them to microwave energy, said apparatus comprising:
    a) a treatment chamber, in which said medical wastes are received and undergo the sterilization process.
    b) a source of microwave energy, substantially a magnetron with a wave-guide for directing the microwaves, emanated by said source to the treatment chamber,
    c) an control and instrumentation means for monitoring the electrical parameters of said power supply means,
    d) an electrical power supply means operatively coupled with the magnetron for energizing the magnetron and establishing microwave radiation emanating therefrom and for energizing the control and instrumentation means,
    e) a liquid medium reservoir, which is in fluid communication with the interior of the treatment chamber, said reservoir is sufficient to supply the liquid medium to the interior of the treatment chamber to produce steam upon exposure the said liquid medium to the microwave energy,
    f) a steam release means, which is in fluid communication with the interior of the treatment chamber, said steam release means is adapted to control pressure within the chamber during the sterilization process,
    wherein said wave-guide comprises a hollow duct communicating with the interior of the treatment chamber, said duct is configured to direct the microwaves produced by the magnetron first in two opposite directions and then in two approaching directions to enable their collision in a meeting point within the treatment chamber.

2. The sterilization apparatus, as defined in claim 1, in which the wave-guide is configured as a body, defined by a mirror symmetry and by a plane of symmetry, wherein said treatment chamber is located with respect to the wave-guide in such a manner, that its plane of symmetry lies in the treatment chamber.

3. The sterilization apparatus, as defined in claim 2, in which said treatment chamber comprises an outer tubular shell, which is receivable within the wave-guide, said shell is provided with at least two opposite through-going windows to enable passing the microwaves therethrough, said shell is lined by a microwave transparent lining.

4. The sterilization apparatus as defined in claim 1, in which said apparatus is provided with a collection bin for collecting the sterilized wastes.

5. The sterilization apparatus as defined in claim 3, in which said treatment chamber is located above the collection bin and is provided with an input door for opening the chamber and loading the wastes thereinto and with an output door for unloading the sterilized wastes therefrom.

6. The sterilization apparatus as defined in claim 4, in which said input door and said output door is operated by a dedicated opening and closing mechanism, said mechanism is constructed to close the respective door so as to seal the treatment chamber.

7. The sterilization apparatus as defined in claim 6 wherein said treatment chamber comprises an outer tubular shell said tubular shell is configured substantially as a cylinder having its longitudinal axis located preferably within the plane of symmetry of the wave-guide.

8. The sterilization apparatus as defined in claim 7, in which said tubular shell is made integral with the wave-guide.

9. A method for sterilization of wastes by exposing them to microwave energy, comprising the following sequence of steps:
   a) placing said wastes within a treatment chamber, configured as microwave-transparent, pressure retaining vessel
   b) hiermetically closing the said treatment chamber
   c) generating of microwaves, substantially by a magnetron source
   d) directing said microwaves through a hollow waveguide from the magnetron source to the interior of the chamber
   e) exposing the wastes placed within the chamber to the microwave energy.
   wherein said microwaves are supplied to the interior of the treatment chamber from two opposite directions to cause their collision within the chamber.

10. The method for sterilization as defined in claim 9, in which directing of the microwaves is carried out along a closed path first in two opposite directions and then in two approaching directions to bring the microwaves approaching the chamber from two opposite sides to collision within the treatment chamber.

* * * * *